(12) United States Patent
Beaglehole

(10) Patent No.: US 7,369,234 B2
(45) Date of Patent: May 6, 2008

(54) METHOD OF PERFORMING OPTICAL MEASUREMENT ON A SAMPLE

(75) Inventor: David Beaglehole, Wellington (NZ)

(73) Assignee: Rudolph Technologies, Inc., Flanders, NJ (US)

( * ) Notice: Subject to any disclaimer, the term of this patent is extended or adjusted under 35 U.S.C. 154(b) by 241 days.

(21) Appl. No.: 10/995,520

(22) Filed: Nov. 24, 2004

(65) Prior Publication Data

US 2005/0134849 A1    Jun. 23, 2005

Related U.S. Application Data

(63) Continuation-in-part of application No. PCT/NZ2004/000010, filed on Jan. 29, 2004.

(30) Foreign Application Priority Data

| Feb. 3, 2003 | (NZ) | ................................ 523937 |
| Aug. 12, 2003 | (NZ) | ................................ 527516 |
| Jun. 4, 2004 | (NZ) | ................................ 533343 |

(51) Int. Cl.
  *G01J 4/02* (2006.01)
  *G02F 1/01* (2006.01)
(52) U.S. Cl. ............... 356/369; 356/366; 356/364; 250/225
(58) Field of Classification Search ................ None
  See application file for complete search history.

(56) References Cited

U.S. PATENT DOCUMENTS

| 5,286,968 A * | 2/1994 | Fournier et al. ......... 250/208.1 |
| 5,501,637 A * | 3/1996 | Duncan et al. ............. 374/126 |
| 5,617,203 A | 4/1997 | Kobayashi et al. |
| 5,757,671 A * | 5/1998 | Drevillon et al. .......... 356/367 |
| 5,838,441 A | 11/1998 | Satorius et al. |
| 5,929,994 A | 7/1999 | Lee et al. |
| 6,134,012 A * | 10/2000 | Aspnes et al. .............. 356/369 |
| 6,608,717 B1 | 8/2003 | Medford et al. |
| 6,714,301 B2 * | 3/2004 | Otsuki et al. ............... 356/369 |
| 6,856,391 B2 * | 2/2005 | Garab et al. ................ 356/366 |
| 6,940,602 B2 * | 9/2005 | Dubois et al. .............. 356/497 |
| 7,064,828 B1 * | 6/2006 | Rovira et al. ............... 356/369 |

OTHER PUBLICATIONS

Full-field optical coherence microscopy, E. Beaurepaire, A. C. Boccara, M. Lebec, L. Blanchot, and H. Saint-Jalmes, Optics Letters vol. 23, Feb. 1998, p. 244-246.*

(Continued)

Primary Examiner—Layla G. Lauchman
Assistant Examiner—Jonathan Skovholt
(74) Attorney, Agent, or Firm—Harrington & Smith, PC

(57) ABSTRACT

The invention relates to a method of performing an optical measurement on a sample, such as an ellipticity measurement. The sample is irradiated with a polarized irradiation beam and a return beam is linearly polarized. The irradiation or return beam is modulated with a birefringence modulator, such as a photoelastic modulator, in accordance with a primary modulation signal. The return beam is directed onto a multichannel detector. Typically the detector is a slow detector, such as a CCD, having a response time greater than a period of the primary modulation signal. Detection values are generated simultaneously at each detection element and processed to determine a plurality of measurements. Various measurement techniques are described, including detector signal averaging over gated intervals; a design employing coherent modulation of the gain of an ICCD, and a modulator-coherent flash lamp design.

35 Claims, 8 Drawing Sheets

OTHER PUBLICATIONS

Real-time reflectivity and topography imagery of depth-resolved microscopic surfaces, A. Dubois, A. C. Boccara, and M. Lebec, Optics Letters, vol. 24, Mar. 1990, p. 309-311.*

Optical Shop Testing, Daniel Malacara, 1978, Wiley, sections 13.1-13.2.*

Charge-coupled device image sensor as a demodulator in a 2-D polarimeter with a piezoelastic modulator, Hanspeter Povel, Hans Aebersold, and Jan O. Stenflo, Applied Optics, vol. 29, No. 8, Mar. 10, 1990, p. 1186-1190.*

The Lock-In CCD—Two Dimensional Synchronous Detection of Light, T. Spirig, P. Seitz, O. Vietze, and F. Heitger, IEEE Journal of Quantum Electronics, vol. 31, No. 9, Sep. 1995, p. 1705-1708.*

Digital Wavefront Measuring Interferometer for Testing Optical Surfaces and Lenses, J. H. Bruning, D. R. Herriott, J. E. Gallagher, D. P. Rosenfeld, A. D. White, and D. J. Brangaccio, Applied Optics, vol. 13, No. 11, Nov. 1974, p. 2693-2703.*

D. Beaglehole, "The Imaging Ellipsometer," Dec. 2003, Salamanca Group, No. 716, p. 2.

D. Beaglehole, "Performance of a microscopic imaging ellipsometer," 1998, Rev. Sci. Instrum. 59(12). 2557. 3 pp.

E. Beaurepaire et al., "Optical coherence microscopy for the in-depth study of biological structures: system based on a parallel detection scheme," SPIE—Proceedings of Optical Biopsy II, 1998, vol. 3250, pp. 201-208.

* cited by examiner

Time (fraction of a cycle)

Time (fraction of a cycle)

(a)

(b)

(c)

(d)

Time (fraction of a cycle)

Time (fraction of a cycle)

METHOD OF PERFORMING OPTICAL MEASUREMENT ON A SAMPLE

This is a Continuation in Part of International Application No. PCT/NZ2004/000010 filed Jan. 29, 2004 the contents of which are hereby incorporated herein by reference.

FIELD OF THE INVENTION

The invention relates to a method of performing an optical measurement on a sample, such as an ellipticity measurement.

BACKGROUND OF THE INVENTION

Ellipsometers have been used for a number of years in measurements of thin films. In particular, ellipsometers have been used in the measurement of oxide and other layers on semiconductors. Ellipsometers analyse the ellipticity induced by reflection from a surface, measuring two parameters. This technique enables much more precise measurements than are possible using reflectometry measurements, for example.

A simple ellipsometer includes a light source which produces a beam of light which passes through a polarizer, forming a beam of light which is plane—polarised or has another well-defined polarisation state. The light source may be a laser or LED for single wavelength measurements, or a white light source for spectroscopic measurements. The beam passes through a retarder (sometimes referred to as a compensator) before striking the surface of a sample. The reflected light passes through a second polarizer (usually called the analyser) and enters a light detector. The light detector is usually a photodiode or a photomultiplier. An ellipsometer with a single photodiode or photomultiplier detector is a single channel ellipsometer.

The retarder may rotate. Alternatively, a birefringence modulator may be used. This modulator is typically a photoelastic modulator which includes an element with a birefringence dependent on the strain applied to it. A periodic strain is applied by a piezoelectric transducer, so that the birefringence is modulated at a high frequency (angular frequency $\omega_0$) usually in a mechanical resonance mode. Retarders may also be liquid crystal polarising devices.

A single channel birefringence-modulator ellipsometer has a sensitivity which is typically 100 times more than that of a common rotating-component ellipsometer. The ellipsometer has one detector. It achieves its very high sensitivity by using coherent lock-in amplifier detection operating at $\omega_0$ and $2\omega_0$. This puts the electronics into a low noise region and the coherent detection of the lock-in with both frequency and phase eliminates noise signals which are not coherent with the modulator. Further, the modulation element undergoes mechanical resonance without motion of the centre of mass, and this eliminates motion of the light beam on the detector which often causes residual stray signals in the rotating-component design.

The usual configuration for a birefringence-modulator ellipsometer is Source, P, M, Sample, A, Detector, where P, M, and A are respectively the Polariser, Modulator and Analyser (sometimes it is used with the modulator following the sample). In the usual configuration the Polariser and Analyser are oriented at 45° and the modulator is parallel or perpendicular to the s direction (the s direction being parallel to the surface of the sample and perpendicular to the plane of incidence). Then $$I=I_0 r_s^2 \{1+\rho^2+2\rho^2 \cos(\Delta+\delta)\} \quad (1)$$

Here $I_0$ is the incident intensity, I the intensity following the Analyser, $r_s$ the magnitude of the s amplitude reflectivity, $\rho$ and $\Delta$ are the parameters of the reflected polarisation ellipse, $\rho$ the magnitude and $\Delta$ the phase angle, $\delta$ the modulator phase shift which varies with time as $\delta=\delta_0 \sin \omega_0 t$. The expression can be expanded to read $$I \propto 1+\rho^2+2\rho \cos \Delta \cos \delta - 2\rho \sin \Delta \sin \delta$$

$$I \propto 1+\rho^2+2\rho \cos \Delta \{J_0(\delta_0)+2J_2(\delta_0)\cos 2\omega_0 t+\ldots\}-2\rho \sin \Delta \{2J_1(\delta_0)\sin \omega_0 t+2J_3(\delta_0)\sin 3\omega_0 t+\ldots\} \quad (2)$$

Here $J_0, J_1, J_2 \ldots$ are integer Bessel Functions dependent on the amplitude of the modulator phase shift $\delta_0$ and the series sums continue to higher order. The three lowest frequency terms are:

the dc component $I_{dc} \propto 1+\rho^2 \cos(\Delta J_0(\delta_0))$ (3)

the ac component at angular frequency $\omega_0$ $I_{\omega 0} \propto 2\rho (\Delta J_1(\delta_0)) \sin \omega_0 t$ (4)

the ac component at angular frequency $2\omega_0$ $I_{2\omega 0} \propto 2\rho \cos(\Delta J_1(\delta_0)) \cos 2\omega_0 t$ (5)

Lock-in amplifiers tuned to $\omega_0$ and $2\omega_0$ output the amplitudes of the $\omega_0$ and $2\omega_0$ signals. The ratios $ac(\omega_0)/dc$ and $ac(2\omega_0)/dc$ provide two expressions for $\rho$ and $\Delta$ from which these two parameters may be obtained. The ratios simplify if $\delta_0$ is chosen so that $J_0(\delta_0)=0$, when $$x = ac(2\omega_o)/dc = \frac{2\rho \cos \Delta}{1+\rho^2}, \quad y = ac(\omega_o)/dc = \frac{2\rho \sin \Delta}{1+\rho^2}.$$

Ellipsometers may be used in an imaging mode, where a multichannel array detector such as a CCD is used. In this case a rotating modulator has been used and a set of CCD images are recorded at different orientations of the retarder, which can then be analysed to form images of x and y, or $\rho$ and $\Delta$, over the illuminated sample area.

It would be desirable to use the beneficial features of a birefringence modulator (high stability modulation and little or no motion of the centre of mass) in such an ellipsometer. The frame rate of multichannel CCD detectors is typically in the range 20 to 200 frames per second, while the modulation frequency $\omega_0$ of a typical birefringence modulator is around 50 kHz. It is not possible to follow the rapidly changing modulated signal using an otherwise suitable detector.

A multi-detector ellipsometer is described in U.S. Pat. No. 5,757,671. The detectors used are photodiodes, with the signals from all detectors being multiplexed to a single analog/digital converter. The signal is subsequently Fourier decomposed. The x and y signals are not measured at the same time. This method is not readily extendable to a large number of channels.

A multichannel or multi-detector spectroscopic ellipsometer based on a birefringence modulator is an example of another desirable instrument. Here multichannel detectors could measure all colours at the same time. A straight forward method to achieve this would consist of many single channels detectors each with their associated two lock-in amplifiers. Such an instrument would be very bulky. Multichannel CCD detectors are again too slow to follow the modulation signals.

SUMMARY OF THE INVENTION

A first aspect of the invention provides a method of performing a measurement on a sample including:
  irradiating the sample with a polarized irradiation beam;
  linearly polarizing a return beam from the sample;
  modulating the irradiation or return beam with a birefringence modulator in accordance with a primary modulation signal;
  generating a secondary modulation signal which has a predetermined phase relationship with the primary modulation signal;
  directing the return beam onto a multichannel detector, the multichannel detector having a plurality of detection elements;
  simultaneously generating a detection value at each detection element;
  processing the simultaneously generated detection values to determine a plurality of measurements, each measurement corresponding with a respective detection element and being indicative of a change induced by the sample on the irradiation beam; and
  modulating the irradiation or return beam in accordance with the secondary modulation signal, or controlling the generation or processing of the detection values in accordance with the secondary modulation signal.

A second aspect of the invention provides measurement apparatus including:
  a radiation source;
  a polarizer;
  a birefringence modulator configured to modulate an irradiation or return beam in accordance with a primary modulation signal;
  an analyzer;
  means for generating a secondary modulation signal which has a predetermined phase relationship with the primary modulation signal;
  a multichannel detector having a plurality of detection elements configured to simultaneously generate a detection value at each detection element;
  a processor for processing the simultaneously generated detection values to determine a plurality of measurements, each measurement corresponding with a respective detection element and being indicative of a change induced by the sample on the irradiation beam; and
  means for modulating the irradiation or return beam in accordance with the secondary modulation signal, or controlling the generation or processing of the detection values in accordance with the secondary modulation signal.

By processing a set of simultaneously generated detection values, the invention provides a truly parallel system which is fast, and is readily extendable to a large number of channels. This can be contrasted with the system of U.S. Pat. No. 5,757,671 in which each detector value is generated at a different time.

In imaging or spectroscopic configurations this enables studies of a substrate to be analysed in a short time. This aspect of the invention is particularly valuable in time-critical processes such as semiconductor manufacture or situations where surface features are changing with time.

The use of a birefringence modulator brings the advantages of relatively high stability modulation and little or no motion of the centre of mass.

Furthermore, the invention performs synchronous illumination or detection using a secondary modulation signal. This enables the modulator and detector/processor to operate synchronously, even when their respective frequencies of operation are different. For instance it enables a "slow" detector to be used, which cannot follow the primary modulation signal, but can integrate the detection signals over portions of the modulator cycle. Such a detector typically has a response time greater than a period of the primary modulation signal, and is typically also an integrating detector. However it should be noted that a "fast" detector may also be employed, and the detection values integrated not by the detector itself, but in subsequent electronics.

The invention also typically avoids the need for conventional lock-in amplifier detector which would be prohibitively bulky and expensive in the number required for say 500 parallel channels.

The use of a secondary modulation signal also provides flexibility, enabling a variety of detection schemes to be employed. Typically the secondary modulation signal switches in turn between two or more measurement modes, although it is possible that the measurement of some useful parameters might be achieved by using only a single measurement mode. However in the preferred schemes described below there are at least three modes including a DC measurement mode.

In some preferred measurement procedures the secondary modulation signal has a first phase relationship with the primary modulation signal during a first measurement mode, and a second phase relationship with the primary modulation signal during a second measurement mode. For example the secondary modulation signal may include a series of pulses having a first phase relationship with the primary modulation signal during the first measurement mode, and a series of pulses having a second phase relationship with the primary modulation signal during the second measurement mode. Alternatively the secondary modulation signal may include a series of pulses with a first pulse width during the first measurement mode, and a series of pulses with a second pulse width during the second measurement mode.

In other preferred measurement procedures the secondary modulation signal has a first frequency content during a first measurement mode, and a second frequency content during a second measurement mode. For example the secondary modulation signal may contain a first set of one or more harmonics of the frequency of the primary modulation signal during the first measurement mode, and a second set of one or more harmonics of the frequency of the primary modulation signal during the second measurement mode. Alternatively the secondary modulation signal may contain a square-wave pulse train at a first frequency during the first measurement mode, and a square-wave pulse train at a second frequency during the second measurement mode.

The secondary modulation signal may be used to control a variety of hardware elements, in order to perform the desired coherent detection. For instance the irradiation or return beam may be modulated by opening and closing a gate in the path of the irradiation beam (see gate 19 in FIG. 11) or the return beam (see a gate comprising an intensifier 11 and phosphor screen 12 in FIG. 1). In a preferred embodiment this is achieved by using an intensified charge-coupled device (ICCD), although any controllable gate (such as a chopper coherent with the modulator) may be used. Alternatively the irradiation beam may be modulated in accordance with the secondary modulation signal by turning on and off a radiation source such as a flash lamp. This has the advantage that the source is only on for some of the time, thus reducing power requirements and extending the life of the source. Alternatively the irradiation beam may be modulated in accordance with the secondary modulation signal by varying the intensity of a radiation source such as a light emitting diode or LED. Alternatively the generation or processing of the detection values may be controlled by varying a gain of the muhichannel detector, or controlling subsequent electronics in accordance with the secondary modulation signal.

In the case where the radiation source is turned on and off to produce a series of radiation pulses, and the spectrum of the pulse varies with time during heating and cooling effects, the method may further include the step of closing a gate in the path of the irradiation or return beam during each radiation pulse, or reducing the gain of the detector during each radiation pulse. This provides a "spectral clean-up" of the radiation pulses by discarding unwanted signal.

Although generated in parallel, the detection values are typically read out serially from the multichannel detector.

In the preferred hardware examples described below the multichannel detector is a Charge Coupled Device (CCD) detector. Alternatively the detector may be a Complementary Metal Oxide Semiconductor (CMOS) detector or a Photo Diode Array (PDA) detector, with suitable gating features.

A variety of birefringence modulators may be used. In the preferred hardware examples described below a resonant modulator such as a photoelastic modulator is used. However, other non-resonant types of birefringence modulator may be used, such as a liquid crystal variable retarder, or Faraday or Kerr effect retarders.

The method may be employed in an imaging device, in which a two dimensional image representative of a property of the sample is provided. Alternatively the apparatus may be used in a spectroscopic mode, where the light incident on the detector is dispersed using a grating (or other wavelength dispersive element) and the measurements are made as a function of wavelength.

The method may be employed to perform a variety of measurements where the measured property is associated with transmission through a sample as well as reflection from a sample. Examples include ellipticity, circular transmission dichroism, stress birefringence and surface optical anisotropy.

BRIEF DESCRIPTION OF THE DRAWINGS

The invention will now be described by way of example with reference to the accompanying drawings, in which.

DESCRIPTION OF THE INVENTION

Figure 5:
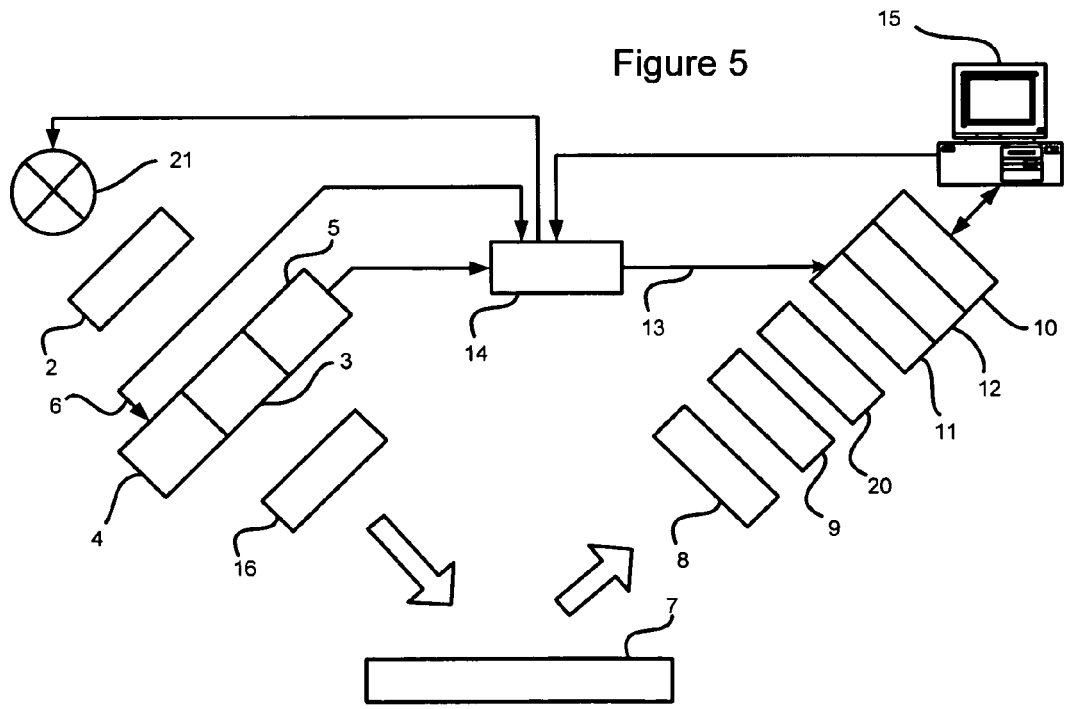
FIG. 5 shows a spectroscopic ellipsometer with a triggered flash lamp.

Various embodiments of the invention will now be described with reference to a first hardware example (FIG. 1) and a second hardware example (FIG. 5).

1 First Hardware Example: Modulator-coherent Detector Signal Integrating Over Gated Intervals of a Modulator Cycle

1.1 Hardware

Figure 1:
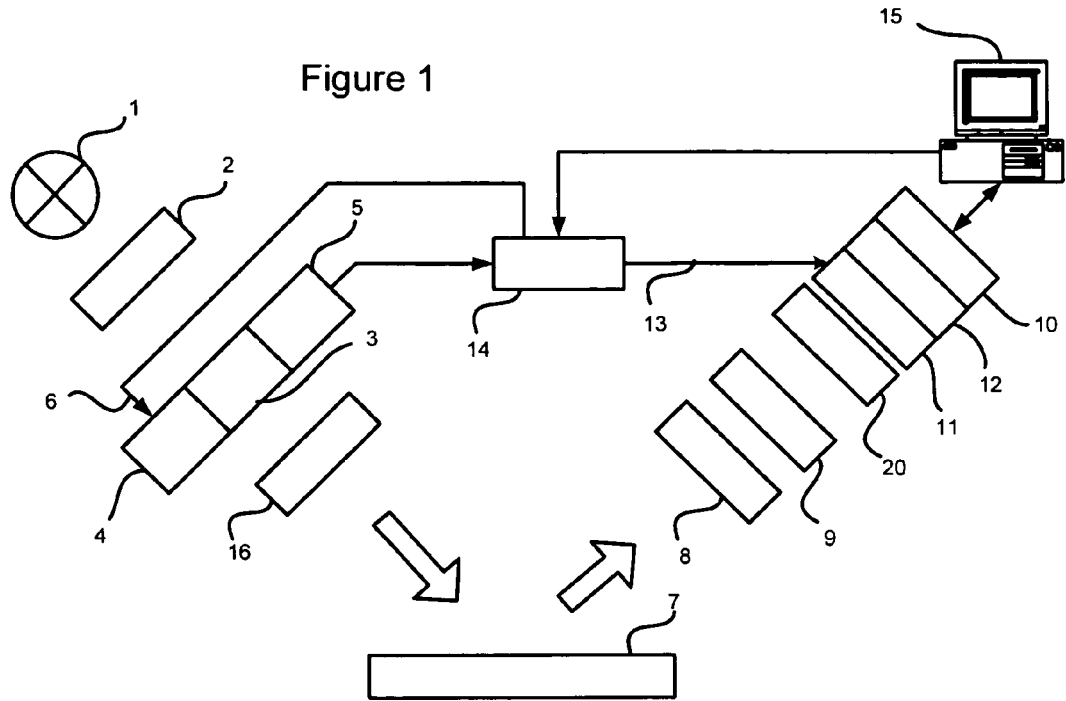
FIG. 1 shows a spectroscopic ellipsometer.

FIG. 1 shows a spectroscopic ellipsometer. Light from a white light source 1 passes through a polarizer 2, forming a beam of plane-polarized light. The polarized beam is modulated by a photoelastic birefringence modulator which comprises a fused silica modulator portion 3 which is driven into resonance by a piezoelectric drive element 4. A piezoelectric gauge element 5 generates a signal in response to the vibration of the modulator portion, and feeds the signal back into the drive element via a feedback path 6. An example of a suitable modulator is the High Stability Birefringence Modulator manufactured by Beaglehole Instruments Limited of 32 Salamanca Road, Wellington, New Zealand.

The beam passes through the modulator and a condenser lens 16, before striking the surface of a sample 7. The reflected light passes through an objective lens 8, a second polarizer 9 (usually called the analyser) and is focused onto the entrance slit of a spectrograph 20 which has an intensified charge-coupled device (ICCD) camera at the exit plane. The ICCD camera has a CCD 10, and a gate in front of the CCD which can be opened and closed in a time ~5 ns (depending upon the manufacturer). The gate comprises an intensifier 11 and phosphor screen 12. The intensifier operates in a similar way to a photomultiplier, and the gain of the intensifier 11 can be controlled via an input line 13. An example of a suitable ICCD camera is the PI_MAX1024 manufactured by Roper Scientific, 3660 Quakerbridge Road, Trenton, N.J. 08619.

Figure 10:
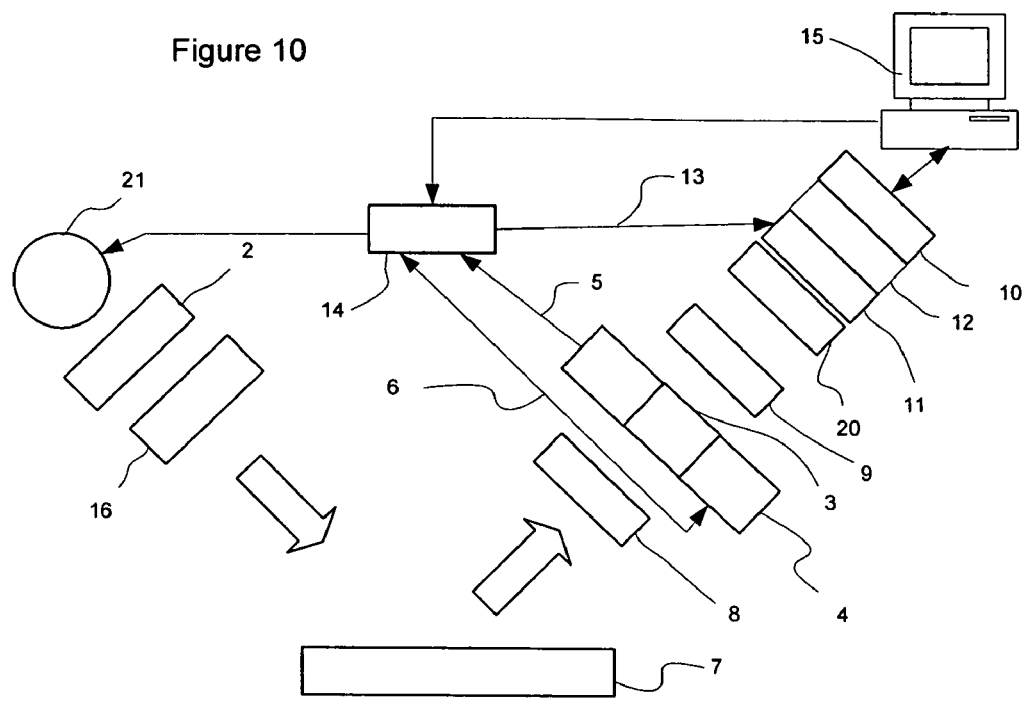
FIG. 10 shows a spectroscopic ellipsometer with a triggered flash lamp.
Figure 11:
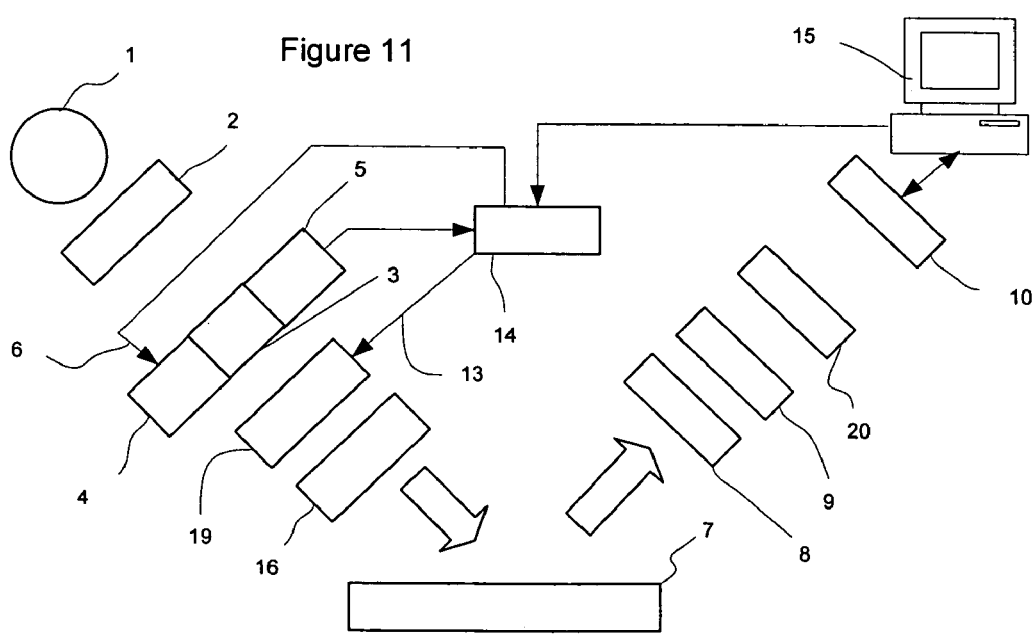
FIG. 11 shows a spectroscopic ellipsometer.

In some ICCD cameras, the phosphor screen 12 and CCD 10 are coupled by optical-fibre cables (not shown). In an alternative arrangement, the birefringence modulator may be placed between the sample and the analyser 9. See FIG. 10.

A gate controller 14 controls the gate, and in turn is controlled by a computer 15 which also receives and processes data from the CCD 10. The gate controller 14 derives modulator-coherent pulses each cycle from a positive-going zero crossing of the primary modulation signal received from the gauge element 5, and opens and closes the gate at specified points during the modulator oscillation. For instance it can be held open for one full period T of the modulator, in which case we measure $$\int_0^T I_{dc} dt,$$

the ac terms averaging to zero. Other intervals for instance 0-T/2, 0-5T/8 give functions of $\rho \cos \Delta$ and $\rho \sin \Delta$, from which $\rho$ and $\Delta$ can be derived. When shot noise limited, the noise of the detector is proportional to the square root of the number of photons falling on the detector during the measurement time, so this number is a measure of the design efficiency. In the present case about ¼ of the photons incident onto the detector are not used, and measurements for three separate intervals are required to determine $I_0$ and the two ellipsometry parameters.

The CCD 10 is read out by computer 15 which processes the data to calculate a set of ellipticity values. The computer 15 may process data from each individual CCD pixel, or may only process summed values taken from blocks of pixels (a technique commonly known as "binning"). Also, the computer may process data taken from the entire CCD, or from only a specified region of interest (ROI) within the field of view of the CCD.

The hardware of FIG. 1 can be operated using a variety of measurement procedures. An ellipsometry analysis is given below for three measurement procedures followed by an example of the measurement procedure.

1.2.1 Ellipsometry Analysis (First Measurement Procedure)

The signal measured in a single channel of a modulation ellipsometer is:

$$I = I_0 r_s^2 \{1 + \rho^2 + 2\rho \cos(\Delta + \delta)\}$$

$$I_0 r_s^2 \{1 + \rho^2 + 2\rho \cos\Delta \cos\delta - 2\rho \sin\Delta \sin\delta\} \quad (6)$$

where $\Delta$ is the optical phase shift due to the sample, and $\delta$ is the optical phase-shift of the modulator, and $\delta = \delta_0 \sin \omega t$.

In the first measurement procedure the signal is integrated between times $t_1$ and $t_2$:

$$\cos\delta = J_o(\delta_o) + 2J_2(\delta_o)\cos 2\omega t + 2J_4(\delta_o)\cos 4\omega t + \ldots \quad (7)$$

$$\int_{t1}^{t2} dt \cos\delta = J_o(\delta_o)(t_2 - t_1) + 2J_2(\delta_o) \int_{t1}^{t2} dt \cos 2\omega t + \quad (8)$$
$$2J_4(\delta_o) \int_{t1}^{t2} dt \cos 4\omega t + \ldots$$
$$= J_o(\delta_o)(t_2 - t_1) + (2J_2(\delta_o)/2\omega)(\sin 2\omega t_2 - \sin 2\omega t_1) + (2J_4(\delta_o)/4\omega)(\sin 4\omega t_2 - \sin 4\omega t_1) + \ldots$$

$$\sin\delta = 2J_1(\delta_o)\sin\omega t + 2J_3(\delta_o)\sin 3\omega t + \ldots \quad (9)$$

$$\int_{t1}^{t2} dt \sin\delta = 2J_1(\delta_o)\int_{t1}^{t2} dt \sin\omega t + 2J_3(\delta_o)\int_{t1}^{t2} dt \sin 3\omega t + \ldots \quad (10)$$
$$= (2J_1(\delta_o)/\omega)(\cos\omega t_1 - \cos\omega t_2) + (2J_3(\delta_o)/3\omega)(\cos 3\omega t_1 - \cos 3\omega t_3) + \ldots$$

$$\int_{t1}^{t2} dt I = I_0 r_s^2 \{1 + \rho^2 + J_0(\delta_o)2\rho\cos\Delta(t_2 - t_1) + \quad (11)$$
$$4\rho\cos\Delta[J_2(\delta_o)/2\omega)(\sin 2\omega t_2 - \sin 2\omega t_1) + (J_4(\delta_o)/4\omega)(\sin 4\omega t_2 - \sin 4\omega t_1) + \ldots] + $$
$$4\rho\sin\Delta[J_1(\delta_o)/\omega)(\cos\omega t_1 - \cos\omega t_2) + (J_3(\delta_o)/3\omega)(\cos 3\omega t_1 - \cos 3\omega t_2) + \ldots]\}$$

The following table presents the values of the three terms normalised by $I_0 r_s^2$ integrated from time t1=0 to time t2: T equals the modulator period $2\pi/\omega$).

$t2 = T/2$

Term 1 $[1+\rho^2+J_0(\delta_0)2\rho \cos \Delta](T/2)$

Term 2 (even J) 0

Term 3 (odd J)

$$4\rho \sin \Delta[2J_1(\delta_0)+2J_3(\delta_0)/3+2J_5(\delta_0)/5+\ldots](T2\pi) \quad (12)$$

$t2 = 5T/8$

Term 1 $[1+\rho^2+J_0(\delta_0)2\rho \cos \Delta](5T/8)$

Term 2 $4\rho \cos \Delta[J_2(\delta_0)/2-J_6(\delta_0)/6](T/2\pi)$

Term 3

$$4\rho \sin \Delta[J_1(\delta_0)1.707+J_3(\delta_0)0.293/3+J_5(\delta_0)0.293/5+\ldots](T/2\pi) \quad (13)$$

$t2 = 3T/4$

Term 1 $[1+\rho^2+J_0(\delta_0)2\rho \cos \Delta](3T/4)$

Term 2 0

Term 3 $4\rho \sin \Delta[J_1(\delta_0)+J_3(\delta_0)/3+J_5(\delta_0)/5+\ldots](T/2\pi) \quad (14)$ $t2 = 7T/8$ Term 1 $[1+\pi^2+J_0(\delta_0)2\rho \cos \Delta](7T/8)$ Term 2 $4\rho \cos \Delta[-J_2(\delta_0)/2+J_6(\delta_0)/6](T/2\pi)$ Term 3

$$4\rho \sin \Delta[J_1(\delta_0)0.293+J_3(\delta_0)1.707/3+J_5(\delta_0)0.293/5+\ldots](T/2\pi) \quad (15)$$

$t2 = T$

Term 1 $[1+\rho^2+J_0(\delta_0)2\rho \cos \Delta]T$

Term 2 0

Term 3

$$0 \quad (16)$$

The terms $\rho \sin \Delta$ and $\rho \cos \Delta$ are the real and imaginary parts of the complex amplitude reflectivity ratio, which fully determine the ellipticity. These can be seen to depend upon $\delta_0$, which in turn depends upon the amplitude of the modulator birefringence, which in turn varies inversely with the optical wavelength. The lowest order Bessel functions dominate the expressions, but the higher orders contribute a little at large $\delta_0$.

To remove the dependence on the intensity we take the ratio of two measurements made for different integration periods. If we take the total signal for t2=3T/4 and divide this by the total signal for t2=T we have the ratio:

$$\frac{I(t1=0, t2=3T/4)}{I(t1=0, t2=T)} = \frac{4\rho\sin\Delta\alpha}{(1+\rho^2+J_0(\delta_0)2\rho\cos\Delta)\beta} \quad (17)$$

where $\alpha$, $\beta$ are simple functions of $\delta_0$ and T.

With a choice of different periods we can similarly get a ratio proportional to $$\frac{4\rho\cos\Delta}{1+\rho^2+J_o 2\rho\cos\Delta} \quad (18)$$

From these ratios the ellipticity parameters can be derived.

1.2.2 Example of First Measurement Procedure

Figure 2:
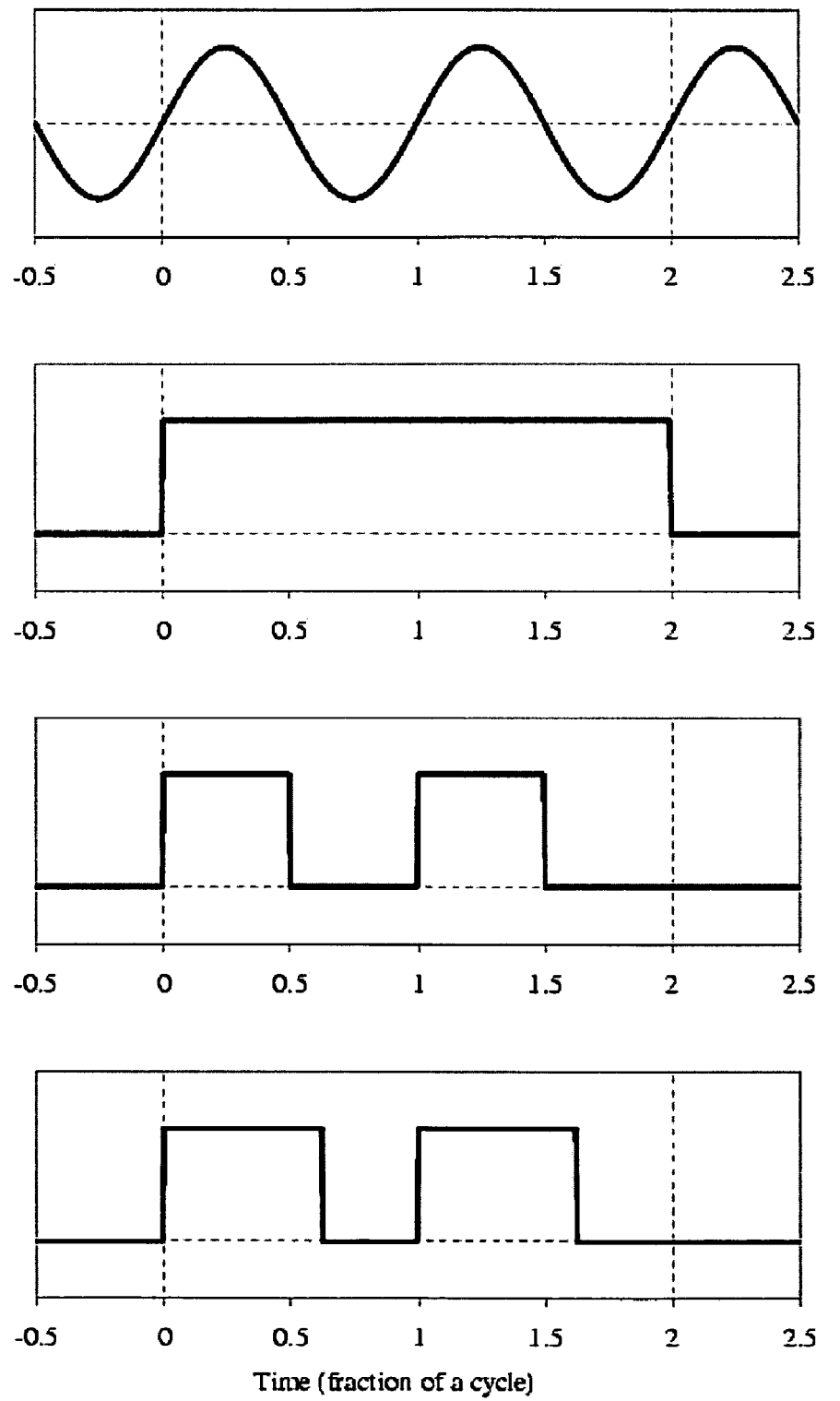
FIG. 2 shows the timing for a first measurement process.

FIG. 2 is a timing diagram of an example of the first measurement procedure. The primary modulation signal is shown in FIG. 2 at (a) as a sine wave at angular frequency $\omega_0$. The gate controller 14 generates a pulse from each positive-going zero crossing of the primary modulation signal, which is used to control the phase of the gate control signal, shown at (b), (c) and (d). The procedure is as follows:

Exposure 1 Fully expose the CCD for $n_1$ cycles of the primary modulation signal. The value $n_1$ is selected so that the CCD is almost fully exposed (pixel wells near full). The gate control signal on input line 13 during Exposure 1 is shown in FIG. 2 at (b). In the example of FIG. 2, $n_1$ is shown with a value of two, so the gate is opened in this case for two cycles Readout 1 Read out the CCD.

Exposure 2 Expose the CCD for $n_2$ cycles of the primary modulation signal, for T/2 seconds per cycle. The value $n_2$ is selected so that the CCD is almost fully exposed, and may be different to the value $n_1$ for Exposure 1. The gate control signal on input line 13 during Exposure 2 is shown in FIG. 2 at (c). In the example of FIG. 2, $n_2$ is shown with a value of two, so the gate is opened in this case for two cycles Readout 2 Read out the CCD.

Exposure 3 Expose the CCD for $n_3$ cycles of the primary modulation signal, for 5T/8 seconds per cycle. The value $n_3$ is selected so that the CCD is almost fully exposed, and may be different to the value $n_1$ for Exposure 1 and/or the value $n_2$ for Exposure 2. The gate control signal on input line 13 during Exposure 3 is shown in FIG. 2 at (d). In the example of FIG. 2, $n_3$ is shown with a value of two, so the gate is opened in this case for two cycles Readout 3 Read out the CCD.

The above steps are then repeated until the noise in the data is as small as desired. The CCD frame readouts are then processed according to the equations above, taking into account appropriately the cycle-exposure numbers $n_1$, $n_2$, $n_3$.

1.3.1 Ellipsometry Analysis (Second Measurement Procedure)

In the second measurement procedure, the gain G is switched between off and G=1 as a square wave as follows:

Odd modulation $G_{odd}=1$ for interval t/T=0 to ½, $G_{odd}=0$ for interval t/T=½ to 1.

Even modulation $G_{even}=0$ for intervals t/T=0 to ⅛, ⅜ to ⅝, ⅞ to 1.=1 for intervals t/T=⅛ to ⅜, ⅝ to ⅞

The total on-time is T/2 each full cycle in both cases. The signal that is measured is the time-averaged product G I over many cycles. Even and odd modulating functions have different averages, classified by their symmetry about T/2.

$$S = I_0 G\{1+\rho^2+2\rho\cos(\Delta+\delta)\} = I_0 G$$

$$\{1+\rho^2+2\rho\cos\Delta\cos\delta - 2\rho\sin\Delta\sin\delta\} \quad (19)$$

We expand the time variation of the modulator optical phase δ:

$$\cos\delta = \cos(\delta_o \sin\omega_o t) = J_o(\delta_o) + \sum_{m=2,4,\ldots} 2J_m(\delta_o)\cos(m\omega_o t) \quad (20)$$

$$\sin\delta = \sin(\delta_o \sin\omega_o t) = \sum_{m=1,3,\ldots} 2J_m(\delta_o)\sin(m\omega_o t)$$

If we average the time-independent terms over one cycle we obtain $S_{dc}$ given by $$S_{dc} = I_0[1+\rho^2+2\rho\cos\Delta J_0]T.$$

If we average the even time-dependent terms for the $G_{even}=1$ on-time, we have $$S_{even} = I_o 2\rho\cos\Delta \int dt \sum_{m=2,4,\ldots} 2J_m(\delta_o)\cos(m\omega_o t)$$

Changing the time variable to $\theta=\omega_0 t=2\pi t/T$ we have $$S_{even} = I_o 2\rho\cos\Delta \frac{T}{2\pi} \sum_{m=2,4,\ldots} 2J_m(\delta_o) \int d\theta \cos(m\theta)$$

$$S_{even} = I_o 2\rho\cos\Delta \frac{T}{2\pi} \sum_{m=2,4,\ldots} 2J_m(\delta_o) \frac{\sin(m\theta)}{m}\Big|_{G_{even}=1}$$

$$S_{even} = I_0 2\rho \cos\Delta T \; Sum_{even} \quad \text{with} \quad Sum_{even} = (-J_2+J_6/3-\ldots)2/\rho \quad (21)$$

Similarly we find using $G_{Odd}$ $$S_{odd} = I_o 2\rho\sin\Delta \int dt \sum_{1,3,\ldots} 2J_m \sin m\omega_o t \quad (22)$$

$$S_{odd} = -I_o 2\rho\sin\Delta \frac{T}{2\pi} \sum_{m=1,3,\ldots} 2J_m \frac{\cos m\theta}{m}\Big|_{G_{odd}=1}$$

$$S_{odd} = I_o 2\rho\sin\Delta T Sum_{odd} \quad \text{with} \quad Sum_{odd}$$
$$= (J_1 + J_3/3 + J_5/5\ldots)2/\pi$$

In our measurements we measure the time integrated signal for $n_1$ full periods with no modulation and obtain the A='dc' signal. We measure with odd modulation and record B='dc'−'odd'. We measure with even modulation and record C='dc'+'even'.

We then have $$\frac{A-B}{A} = \frac{2\rho\sin\Delta Sum_{odd}}{1+\rho^2+2\rho\cos\Delta J_o} = y',$$

$$\frac{C-A}{A} = \frac{2\rho\cos\Delta Sum_{even}}{1+\rho^2+2\rho\cos\Delta J_o} = x'$$

The parameters x, y can be derived from (x', y'):

$$y' = \frac{y Sum_{odd}}{1+xJ_o}, \quad x' = \frac{x Sum_{even}}{1+xJ_o}, \quad (23)$$

$$x = \frac{x'}{Sum_{even} - x'J_o}, \quad y = y'\frac{(1+xJ_o)}{Sum_{odd}} \quad (24)$$

1.3.2 Example of Second Measurement Procedure

Figure 3:
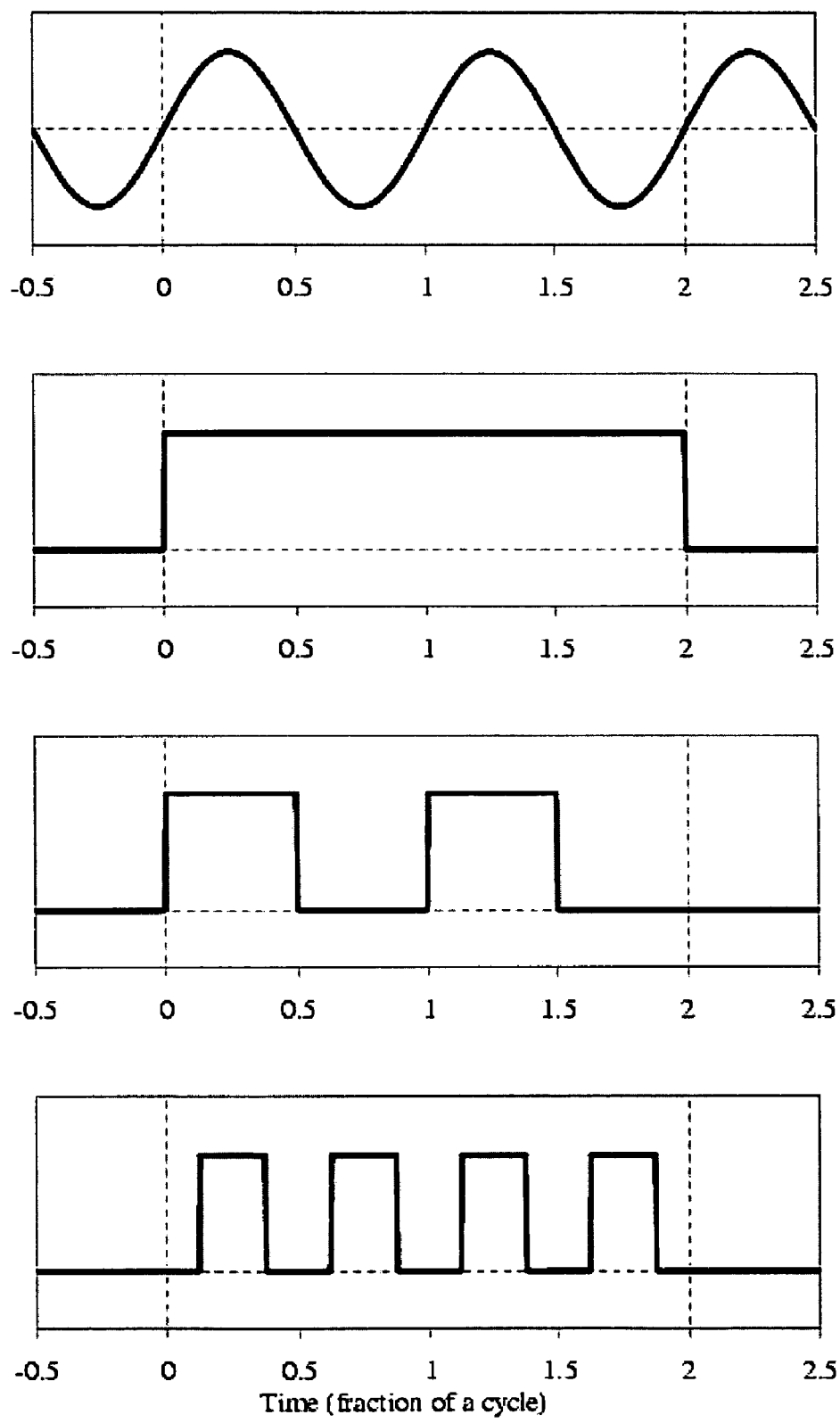
FIG. 3 shows the timing for a second measurement process.

FIG. 3 is a timing diagram of an example of the second measurement procedure. The procedure is as follows:

Exposure 1 Fully expose the CCD for $n_1$ cycles of the primary modulation signal. The value n is selected so that the CCD is almost fully exposed. The gate control signal on input line 13 during Exposure 1 is shown in FIG. 3 at (b). In the example of FIG. 3, $n_1$ is shown with a value of two, so the gate is opened in this case for two cycles Readout 1 Read out the CCD.

Exposure 2 Expose the CCD for $n_2$ cycles of the primary modulation signal, with a square wave at frequency $\omega_0$, odd about $t=T/2$. The value $n_2$ is selected so that the CCD is almost fully exposed, and may be different to the value $n_1$ for Exposure 1. The gate control signal on input line 13 during Exposure 2 is shown in FIG. 3 at (c). In the example of FIG. 3, $n_2$ is shown with a value of two, so the gate is opened in this case for two cycles Readout 2 Read out the CCD.

Exposure 3 Expose the CCD for $n_3$ cycles of the primary modulation signal, with a square wave at frequency $2\omega_0$, even about $t$-$T/2$. The value $n_3$ is selected so that the CCD is almost fully exposed, and may be different to the value $n_1$ for Exposure 1 and/or the value $n_2$ for Exposure 2. The gate control signal on input line 13 during Exposure 3 is shown in FIG. 3 at (d). In the example of FIG. 3 $n_3$ is shown with a value of two, so the gate is opened in this case for two cycles Readout 3 Read out the CCD.

The above steps are then repeated as before until the signal fluctuations are as small as desired.

1.3.3 Experimental Data

Figure 7:
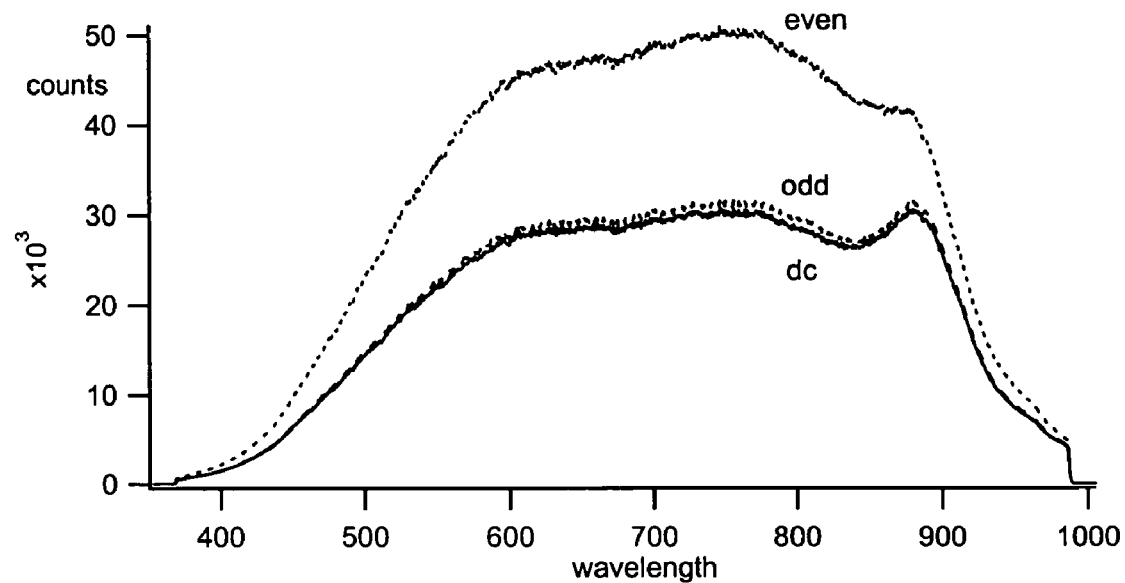
FIG. 7 is a graph showing preliminary data.

FIG. 7 shows some preliminary measurements of the parameters x,y using the second measurement procedure. Note that the polariser and analyzer are only efficient in the range 420 to 800 nm. y~1, x~0 at 630 nm.

Figure 8:
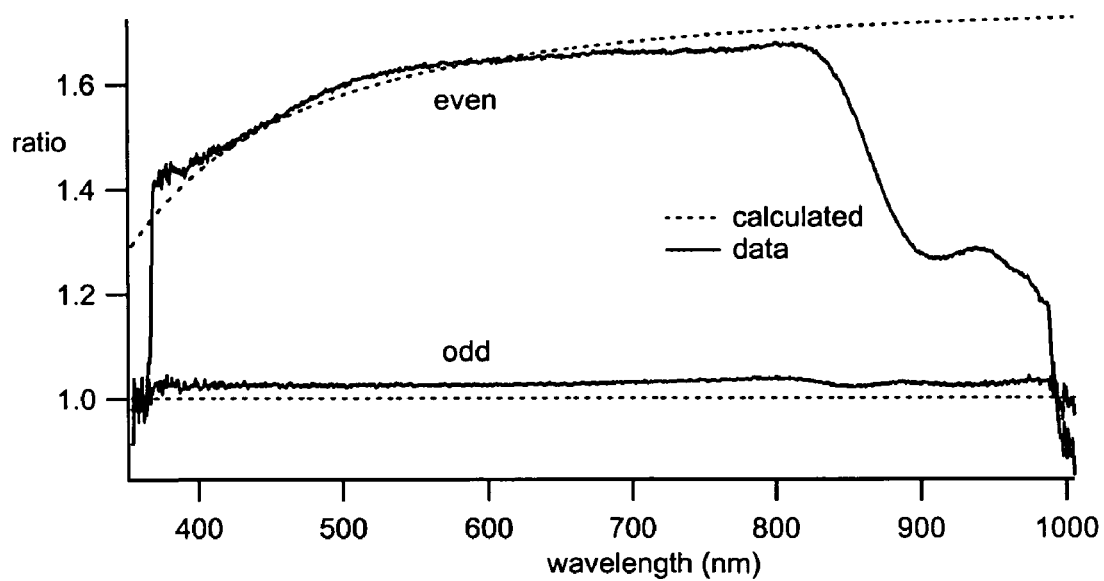
FIG. 8 is a graph showing normalised data.

FIG. 8 is a graph showing normalised data. The solid upper curve shows the even data divided by dc and the lower solid curve shows the odd data divided by dc. The broken lines show calculated values for comparison purposes.

1.4.1 Ellipsometry Analysis (Third Measurement Procedure)

Rather than using a square modulation gate, the intensifier can be used to modulate the gain G of the detector, with the Gain varying in time as the sum of even and odd harmonic sine waves.

If the gain is modulated as $\frac{1}{2}G_0\{1+\cos(\omega_g t+\phi_g)\}$, the signal becomes $$I=\tfrac{1}{2}G_0I_0r_s^2\{1+\cos(\omega_g t+\phi_g)\}\{1+\rho^2+2\rho\cos(\Delta+\delta)\} \quad (25)$$

When the equation is expanded, one half the intensity takes the same dc and ac expressions as before, the other half involves sum and difference terms with angular frequency $\omega_g\pm\omega_0$, $\omega_g\pm 2\omega_0$. Thus if $\omega_g$ is set to 0, $\omega_o$, $2\omega_0$ in turn, the difference frequency becomes zero for each of the dc and ac, and time averaged measurements of the three zero-frequency signals can be made. Note the gain-modulation signal is derived from the modulation oscillation amplitude so that it is exactly coherent. The efficiency is about $\frac{1}{3}$. The gain phase-shift $\phi_g$ can be adjusted for maximum zero-frequency signal. The third measurement procedure effectively turns the detector into a self-operating lock-in amplifier.

The gain-modulating function can also be generated to have equal amplitudes of even and odd higher harmonics:

$$G_{odd}=\tfrac{1}{2}G_0\{(1+\cos\omega_0 t+\cos 3\omega_0 t+\cos 5\omega_o t\ldots\}$$

$$G_{even}=\tfrac{1}{2}G_0\{(1+\cos 2\omega_0 t+\cos 4\omega_0 t+\cos 6\omega_0 t\ldots\} \quad (26)$$

The zero-frequency terms will then be derived from the even and odd harmonics in the ac, dc terms in equations 3, 4, 5 above, giving the zero-frequency signals proportional to $$odd=2\rho\sin\Delta\{J_1(\delta_0)+J_3(\delta_0)+\ldots\}$$

$$even=2\rho\cos\Delta\{J_2(\delta_0)+J_4(\delta_0)+\ldots\} \quad (27)$$

At fixed modulator amplitude $\delta_0$ is a function of light wavelength, and if a wide spectral range is used, zeros in the $J_1, J_2, \ldots$ Bessel functions in equations 3, 4 cause low sensitivity to $\rho$, $\Delta$ in these regions. The sum of the Bessel functions in equation 8 has no zeros, and the "dead" regions can be eliminated. The efficiency is again about $\frac{1}{3}$.

Instead of varying the gain of the detector, one can equivalently vary the intensity of the light source. An LED is a bright and essentially incoherent source and can provide suitably narrow band source for imaging ellipsometry applications. Laser diodes can also be modulated at high frequency, but the longer coherence length makes these less suitable for imaging applications. LED illumination does not have the same coherence.

1.4.2 Example of Third Measurement Procedure

Figure 4:
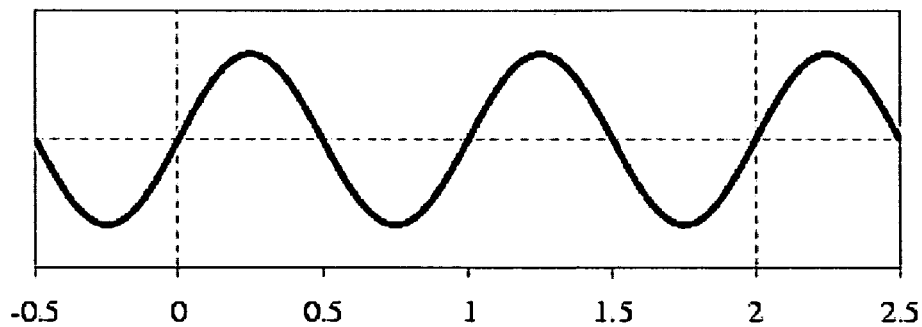
FIG. 4 shows the timing for a third measurement process.
Figure 4:
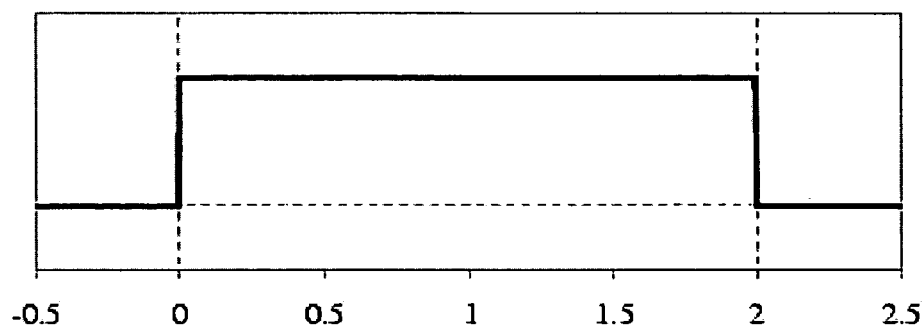
Figure 4:
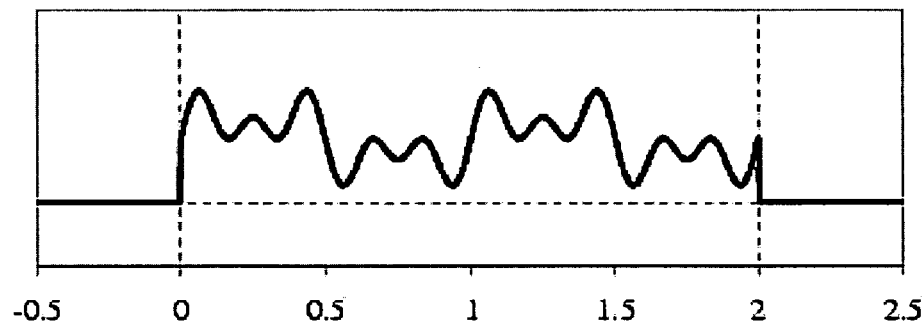
Figure 4:
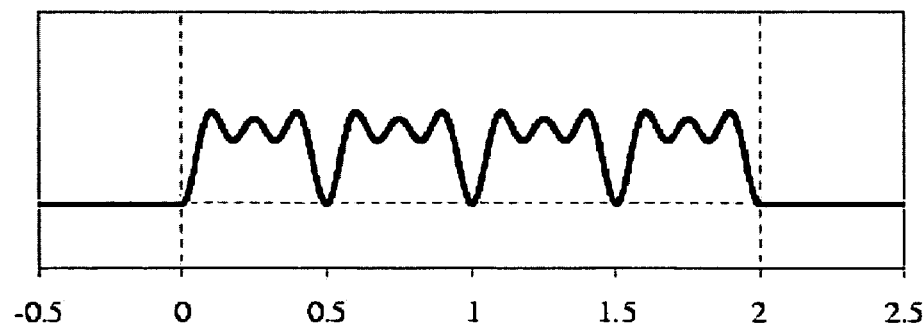

FIG. 4 give an example of the third measurement procedure. The procedure is as follows:

Exposure 1 Fully expose the CCD for $n_1$ cycles of the primary modulation signal. The value $n_1$ is selected so that the CCD is almost fully exposed. The gate control signal on input line 13 during Exposure 1 is shown in FIG. 2 at (b). In the example of FIG. 4, $n_1$ is shown with a value of two, so the gate is modulated in this case for two cycles Readout 1 Read out the CCD.

Exposure 2 Expose the CCD for $n_2$ cycles of the primary modulation signal, with the gain modulated with the sum of three odd sines, odd about $t=T/2$ as shown at (c) in FIG. 4. The value $n_2$ is selected so that the CCD is almost fully exposed, and may be different to the value $n_1$ for Exposure 1. In the example of FIG. 4, $n_2$ is shown with a value of two, so the gate is opened in this case for two cycles Readout 2 Read out the CCD.

Exposure 3 Expose the CCD for $n_3$ cycles of the primary modulation signal, with the gain modulated with the sum of three even sines, even about $t=T/2$ as shown at (d) in FIG. 4. The value $n_3$ is selected so that the CCD is almost fully exposed, and may be different to the value $n_1$ for Exposure 1 and/or the value $n_2$ for Exposure 2. In the example of FIG. 4, $n_3$ is shown with a value of two, so the gate is modulated in this case for two cycles Readout 3 Read out the CCD.

The above steps are then repeated.

2 Second Hardware Example: Coherent Short Flash Lamp Pulse Illumination

2.1 Hardware

An alternative spectroscopic ellipsometer is shown in FIG. 5. Much of the hardware is identical to the hardware shown in FIG. 1, so reference numbers are repeated for identical components.

The conventional light source 1 is replaced by a flash lamp 21 such as a Hamamatsu Super-quiet 15 W Xe Flash tube that generates a pulse with width ~1.75 μs at full width half maximum (FWHM). Each flash provides 0.15 J of energy. The lamp can provide 100 flashes per second. The lamp has an arc size of 1.5 mm. The period of the modulator T is 20 μs, so we will assume in the following analysis that as a first approximation the pulse width is small compared with the period. A more detailed analysis can take into account the finite width.

The xenon arc lamp 21 can be operated in a triggered pulse mode, producing pulses with a maximum repetition frequency ~100 Hz. For instance, if we take measurements at four different points during the cycle, at $t/T=0, \frac{1}{4}, \frac{1}{2}, \frac{3}{4}$, then $I_0, \delta_0, \rho$ and $\Delta$ can be derived. The time-averaged intensity of the flash lamp is less than a 75 W CW Xe lamp through most of the visible spectrum, but has more deep UV light. The efficiency is higher than the averaging mode in the first embodiment described above.

2.1.1 Ellipsometry Analysis

The signal measured in a single channel of a modulation ellipsometer is:

$$I = I_0 r_s^2 \{1 + \rho^2 + 2\rho \cos(\Delta + \delta)\}$$

$$\{1 + \rho^2 + 2\rho \cos\Delta \cos\delta - 2\rho \sin\Delta \sin\delta\} \quad (28)$$

where $\Delta$ is the optical phase shift due to the sample, and $\delta$ is the optical phase-shift of the modulator, and
$\delta = \delta_0 \sin \omega t$ (which varies with wavelength as $\sim C/\lambda$).

If we measure for short times, then we record I at specific values of $\omega t$, for instance as shown in the following Table.

|   | $\omega t$ | $\delta$ | $I/I_0 r_s^2$ |
|---|---|---|---|
| A | 0 | 0 | $1 + \rho^2 + 2\rho\cos\Delta$ |
| B | $\pi/2$ | $\delta_o$ | $1 + \rho^2 + 2\rho\cos\Delta\cos\delta_o - 2\rho\sin\Delta\sin\delta_o$ |
| C | $\pi$ | 0 | $1 + \rho^2 + 2\rho\cos\Delta$ |
| D | $3\pi/2$ | $-\delta_o$ | $1 + \rho^2 + 2\rho\cos\Delta\cos\delta_o + 2\rho\sin\Delta\sin\delta_o$ |

If we take 4 measurements of the intensity at $\omega t = 0$, $\rho/2$, $\rho$ and $3\rho/2$, we can determine the following ratios:

$$y' = \frac{(D-B)}{(D+B)} = \frac{2\rho\sin\Delta\sin\delta_o}{1 + \rho^2 + 2\rho\cos\Delta\cos\delta_o} \quad (29)$$

$$x' = \frac{(A+C)-(B+D)}{(D+B)} = \frac{2\rho\cos\Delta(1-\cos\delta_o)}{1 + \rho^2 + 2\rho\cos\Delta\cos\delta_o} \quad (30)$$

Note the denominators could be A+C which removes the $\cos \delta_0$ term, but makes the linear contribution larger. It is best to work with $\delta_0 = \rho/2$ and $\cos \delta_0 = 0$, but the wavelength variation of $\delta_0$ prevents this for all wavelengths.

Note $$\tan\Delta = \frac{(D-B)}{(A+C)-(B+D)} \frac{(1-\cos\delta_o)}{\sin\delta_o} = \quad (31)$$

$$\frac{(D-B)}{(A+C)-(B+D)}\tan(\delta_o/2)$$

The functions (x', y') are close to the usual modulation ellipsometry functions (x, y) and the latter can be derived directly from (x', y'), the scaling depending on $\delta_0$ and x'.

$$x = \frac{x'}{1-\cos\delta_o(1+x')}, \quad y = \frac{y'\tan(\delta_o/2)}{1-\cos\delta_o(1+x')} \quad (32)$$

Note resonances occur when $\cos \delta_0(1+x')=1$, and for y also when $\delta_0 = \rho$. Between these resonances there is a range of a factor of three where the x', y' measured parameters could be accurately corrected.

Note the B and D measurements can be made at other phases, eg $\rho/4$; the value of $\delta$ would then be $\delta_0/\sqrt{2}$, and the range of sensitivity will be correspondingly altered.

2.1.2 Spectral Clean-up

The intensity that is emitted by the flash lamp is a pulse of light of short duration, set-off by an electric trigger pulse. There is usually a tail which decays slowly following the main flash. This tail has a light spectrum which differs from the spectrum emitted by the main flash. Optical signals which depend upon the spectrum thus will have a time dependence due to changes in the spectrum as well as the primary change associated with the time-varying intensity.

The spectrum changes can be eliminated if only the main portion of the flash is studied. A relatively simple way to eliminate the effects of the tail is to use a gated detector under the control of the same trigger that sets off the flash. There is usually some steady delay between the generation of the flash trigger pulse and the occurrence of the flash. This same trigger pulse can therefore be used to open and close the gate to the detector.

The gate controller 14 opens the intensifier 11 before the flash occurs. The intensifier can then be closed after a time interval chosen so that the intensifier is closed immediately following the main flash, thus eliminating the detection of the tail. This method has been shown to work well in practice. The gating interval was adjusted for the particular delays associated with the flash-intensifier combination by recording the integrated detector signal due to the flash, and then shortening the interval to gate closure until the integrated signal started to fall. We observed a clean-up of signal occurring when the integrated intensity was reduced by a factor of ~10% by shortening the time to the closure of the intensifier.

Adding an intensifier to a CCD is an expensive option, since intensifier technology depends upon high speed switching of high voltages. Some CCDs (eg interline transfer) are able to perform exposure control down to time intervals as short as 10 microseconds. Therefore, instead of using the ICCD shown in FIG. 5, these cameras can therefore be used without requiring an intensifier, if the electronics has accurate timing to (i) start the exposure, (ii) send the flash trigger, (iii) stop the exposure at the appropriate time to cut off the tail. The timing will need careful adjustment to match the particular flash/camera combination but the adjustment so that the flash occurs in the final portion of the exposure interval should be readily achieved.

2.1.3 Example Procedure

Figure 6:
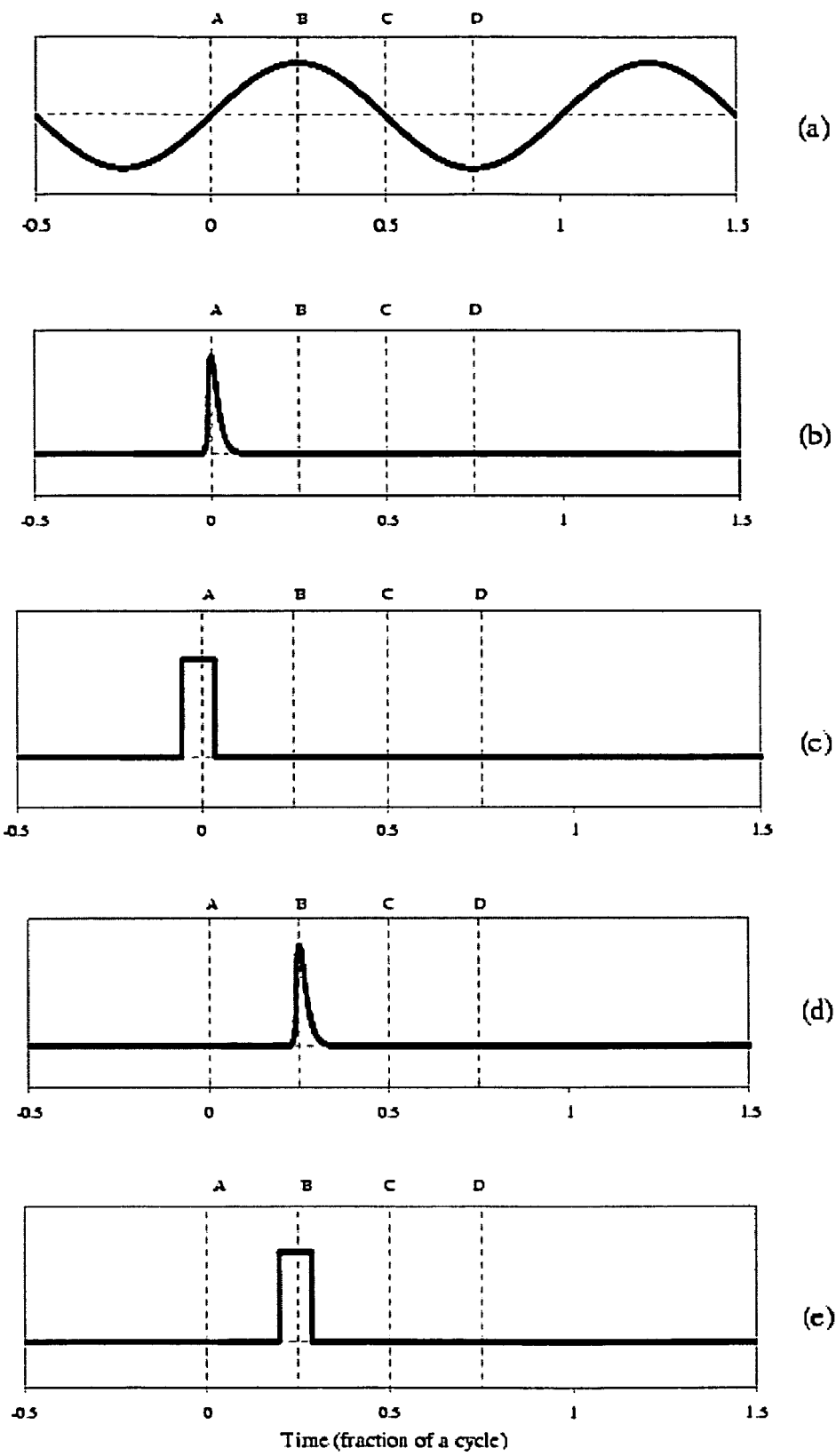
FIG. 6 shows the timing for a fourth measurement process.

FIG. 6 gives an illustrative example of the operation of the system of FIG. 5. The gate controller 14 controls the phase of the flash lamp and gate control signals as shown at (b) to (e).

The procedure is as follows:

Exposure 1 Expose the CCD with n flashes of the flash lamp at phase point A. The flash lamp can typically be flashed at a rate in the range of 100-300 Hz. The value n is selected so that the CCD is almost fully exposed. The output of the flash lamp during only one of the flashes of Exposure 1 is shown at (b), and the gate control signal is shown at (c). The value n might typically take a value of two or three.

Readout 1 Read out the CCD.

Exposure 2 Expose the CCD with n flashes of the flash lamp at phase point B. The output of the flash lamp during only one of the flashes of Exposure 2 is shown at (d), and the gate control signal is shown at (e).

Readout 2 Read out the CCD.

Exposure 3 Expose the CCD with n flashes of the flash lamp at phase point C. The flash lamp output and gate control signal during Exposure 3 are not shown in FIG. 6.

Readout 3 Read out the CCD.

Exposure 4 Expose the CCD with n flashes of the flash lamp at phase point D. The flash lamp output and gate control signal during Exposure 4 are not shown in FIG. 6.

Readout 4 Read out the CCD.

The above steps are then repeated.

2.1.4 Experimental Data

Figure 9:
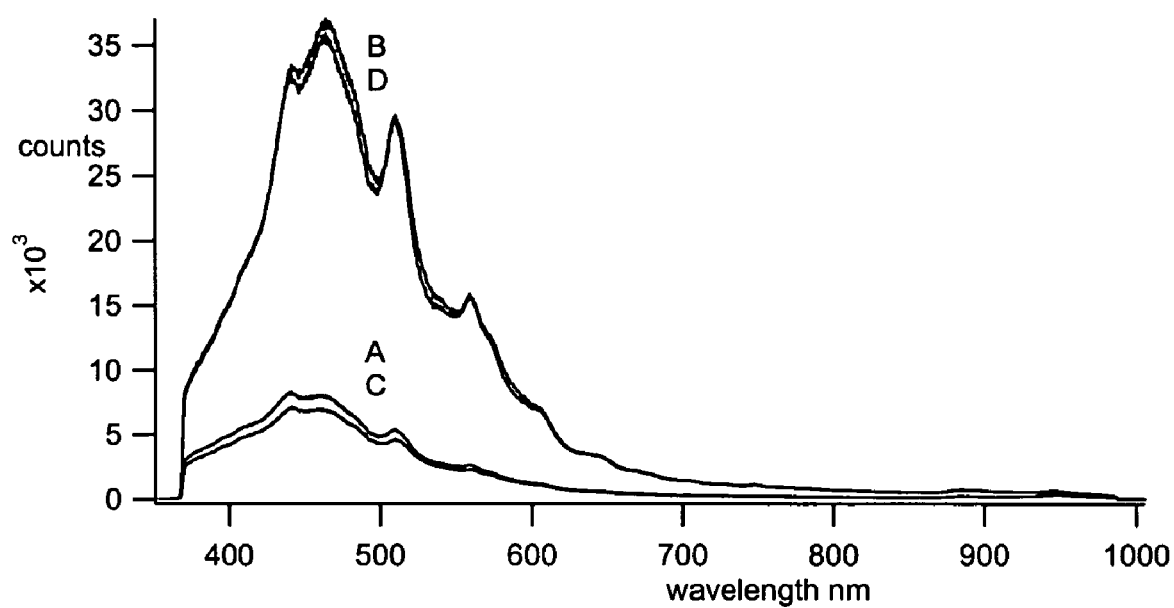
FIG. 9 is a graph showing spectroscopic raw data using a triggered flash lamp method.

FIG. 9 is a graph showing spectroscopic raw data using the triggered flash lamp method.

3 Applications 3.1 Spectroscopic Ellipsometer

In the examples previously described, the invention is employed in a spectroscopic ellipsometer. The spectroscopic ellipsometer included a spectrograph 20 which disperses the return beam across the surface of the ICCD, so that each pixel records intensity at its associated wavelength.

3.2 Imaging Ellipsometer

In this application the sample is illuminated by a condenser, and an objective lens then forms an image of the sample on the multichannel CCD or ICCD. The ellipticity parameters may then be found for each point in the image using one or other of the procedures described above The computer can calculate the ellipticity parameters in a desired region of interest (ROI) or over the whole image field, and display the ellipticity parameters in a desired format. For example an ellipticity parameter x or y may be represented in a gray scale image, with the brightness of each pixel in the image being representative of the value of the parameter at that point on the sample surface.

4 Improved Measurement Method

The measurement methods described above all use a polariser and analyser held with a fixed orientation to the plane of incidence of the light beam. The intensity of light falling on the detector is then given by equation 1 above. This expression assumes that the polariser angle P and the analyser angle R are both 45° to the s direction. If they are at some other angle then ρ must be replaced by the expression $\rho' = \rho \tan R \tan P$, and then it can be seen that if one first measures at angle R, and then measures again at an angle $-R$, $\rho' = -\rho$. Thus one can use the switching of R to $-R$, or equivalently of P to $-P$, to switch the sign of ρ. This simplifies x',y' in many of the new expressions above.

Consider for instance the Second Hardware Example: Coherent short flash pulse illumination. The analysis above used fixed angles of Analyser and Polariser, and expressions for $$y' = \frac{(D-B)}{(D+B)} = \frac{2\rho \sin\Delta \sin\delta_o}{1+\rho^2+2\rho\cos\Delta\cos\delta_o} = \frac{y\sin\delta_o}{1+x\cos\delta_o} \quad (29)$$

$$x' = \frac{(A+C)-(B+D)}{(D+B)} = \frac{2\rho\cos\Delta(1-\cos\delta_o)}{1+\rho^2+2\rho\cos\Delta\cos\delta_o} = \frac{x(1-\cos\delta_o)}{1+x\cos\delta_o} \quad (30)$$

The expression for y' now has a term involving x in the denominator, and both expressions include $\delta_0$ terms which vary with wavelength.

The improved method consists of taking a second set of measurements (subscript 2) along with the first (subscript 1) such that $\tan R_2 \tan P_2 = -\tan R_1 \tan P_1$. The $A_2$ intensity in the table above (see section 2.1.1) becomes $1+\rho^2-2\rho \cos \Delta$. With $A_{sum}=A_1+A_2$ we have $A_{sum}=2(1+\rho^2)$ and $A_{dif}=A_1-A_2$ we have $A_{dif}=4\rho \cos \Delta$, so that $$\frac{A_{dif}}{A_{sum}} = x.$$

Similarly $$\frac{B_{dif}}{A_{sum}} = y\sin\delta_o.$$

While $\delta_0$ depends upon wavelength, these expressions lead more directly than the previous expressions of section 2.1.1 to (x, y).

This method can be applied to all measurement methods described above, and in general the advantages of this method are a much cleaner analysis. The disadvantage is the requirement for twice the number of measurements, but these all contribute to an improvement in the accuracy.

5 Summary

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

The invention claimed is:

1. A method of performing a measurement on a sample to determine a thickness of a film on the sample including:
    irradiating the sample with a polarized irradiation beam;
    linearly polarizing a return beam from the sample;
    modulating the irradiation or return beam with a birefringence modulator in accordance with a primary modulation signal;
    generating a secondary modulation signal which has a predetermined phase relationship with the primary modulation signal;
    directing the return beam onto a multichannel detector, the multichannel detector having a plurality of detection elements;
    simultaneously generating a detection value at each detection element;
    processing the simultaneously generated detection values to determine a plurality of measurements, each measurement corresponding with a respective detection element and being indicative of a change induced by the film on the sample on the irradiation beam;
    modulating the irradiation or return beam in accordance with the secondary modulation signal, or controlling the generation or processing of the detection values in accordance with the secondary modulation signal; and
    using at least the plurality of measurements to determine the thickness of the film.

2. A method according to claim 1 wherein the secondary modulation signal alternates in turn between two or more measurement modes.

3. A method according to claim 2 wherein the secondary modulation signal has a first phase relationship with the primary modulation signal during a first measurement mode; and a second phase relationship with the primary modulation signal during a second measurement mode.

4. A method according to claim 3 wherein the secondary modulation signal includes a series of pulses having a first phase relationship with the primary modulation signal during the first measurement mode; and a series of pulses having a second phase relationship with the primary modulation signal during the second measurement mode.

5. A method according to claim 2 wherein the secondary modulation signal includes a series of pulses with a first pulse width during the first measurement mode; and a series of pulses with a second pulse width during the second measurement mode.

6. A method according to claim 2 wherein the secondary modulation signal has a first frequency content during a first measurement mode; and a second frequency content during a second measurement mode.

7. A method according to claim 6 wherein the secondary modulation signal contains a first set of one or more harmonics of the frequency of the primary modulation signal during the first measurement mode; and a second set of one or more harmonics of the frequency of the primary modulation signal during the second measurement mode.

8. A method according to claim 6 wherein the secondary modulation signal contains a square-wave pulse train at a first frequency during the first measurement mode; and a square-wave pulse train at a second frequency during the second measurement mode.

9. A method according to claim 2 wherein the secondary modulation signal switches in turn between three or more measurement modes.

10. A method according to claim 2 wherein one of the measurement modes is a DC measurement mode.

11. A method according to claim 1 wherein the irradiation or return beam is modulated in accordance with the secondary modulation signal by opening and closing a gate in the path of the beam.

12. A method according to claim 1 wherein the irradiation beam is modulated in accordance with the secondary modulation signal by turning on and off a radiation source.

13. A method according to claim 12 wherein the radiation source is a flash lamp source.

14. A method according to claim 12 wherein the radiation source is a gas discharge lamp.

15. A method according to claim 12 wherein the radiation source is turned on and off to produce a series of radiation pulses, and wherein the method further includes the step of closing a gate in the path of the irradiation or return beam during each radiation pulse, or reducing the gain of the detector during each radiation pulse.

16. A method according to claim 1 wherein the irradiation beam is modulated in accordance with the secondary modulation signal by varying the intensity of a radiation source.

17. A method according to claim 16 wherein the radiation source is a light emitting diode.

18. A method according to claim 1 wherein the generation or processing of the detection values is controlled by varying a gain of the multichannel detector in accordance with the secondary modulation signal.

19. A method according to claim 1 wherein the multichannel detector is an integrating detector.

20. A method according to claim 1 further including serially reading out the detection values from the multichannel detector.

21. A method according to claim 1 wherein the multichannel detector is a charge coupled device.

22. A method according to claim 1 wherein the multichannel detector has a response time greater than a period of the primary modulation signal.

23. A method according to claim 1 further including:
generating a plurality of sets of detection values, each set of detection values corresponding to a different predetermined phase of the birefringence modulator.

24. A method according to claim 1 wherein the birefringence modulator is a photoelastic modulator.

25. A method according to claim 1 wherein the birefringence modulator is a resonant modulator.

26. A method according to claim 1 further including displaying a two dimensional image representative of the measurements.

27. A method according to claim 1 further including directing the return beam onto a wavelength dispersive element.

28. A method according to claim 1 wherein each measurement includes an ellipticity measurement.

29. A measurement apparatus for determining a characteristic of a sample including:
a radiation source for directing an irradiation beam onto the sample;
a polarizer positioned between the radiation source and the sample such that the irradiation beam passes therethrough;
a birefringence modulator configured to modulate one of the irradiation beam or a return beam that is reflected from the sample, the birefringence modulator being modulated in accordance with a primary modulation signal;
an analyzer positioned in the return beam between the sample and a multichannel detector;
means for generating a secondary modulation signal which has a predetermined phase relationship with the primary modulation signal;
the multichannel detector having a plurality of detection elements configured to simultaneously generate a detection value at each detection element, the multichannel detector positioned to have incident thereon at least a portion of the return beam;
a processor for processing the simultaneously generated detection values to determine a plurality of measurements, each measurement corresponding with a respective detection element and being indicative of a change induced by the characteristic of the sample on the irradiation beam;
means for modulating the irradiation or return beam in accordance with the secondary modulation signal, or controlling the generation or processing of the detection values in accordance with the secondary modulation signal; and
wherein the processor is further configured to determine, using at least the plurality of measurements, the characteristic of the sample.

30. A method of measuring a film thickness on a sample including:
providing an apparatus comprising:
a radiation source;
a polarizer;

a birefringence modulator configured to modulate an irradiation or return beam in accordance with a primary modulation signal;

an analyzer;

means for generating a secondary modulation signal which has a predetermined phase relationship with the primary modulation signal;

a multichannel detector having a plurality of detection elements configured to simultaneously generate a detection value at each detection element;

a processor for processing the simultaneously generated detection values to determine a plurality of measurements, each measurement corresponding with a respective detection element and being indicative of a change induced by the sample on the irradiation beam; and means for modulating the irradiation or return beam in accordance with the secondary modulation signal, or controlling the generation or processing of the detection values in accordance with the secondary modulation signal;

irradiating the sample with a polarized irradiation beam;

linearly polarizing a return beam from the sample;

modulating the irradiation or return beam with a birefringence modulator in accordance with a primary modulation signal;

generating a secondary modulation signal which has a predetermined phase relationship with the primary modulation signal;

directing the return beam onto a multichannel detector, the multichannel detector having a plurality of detection elements;

simultaneously generating a detection value at each detection element;

processing the simultaneously generated detection values to determine a plurality of measurements, each measurement corresponding with a respective detection element and being indicative of a change induced by the film on the sample on the irradiation beam;

modulating the irradiation or return beam in accordance with the secondary modulation signal, or controlling the generation or processing of the detection values in accordance with the secondary modulation signal; and determining, using at least the plurality of measurements, the thickness of the film.

31. A method of measuring a film thickness on a sample, including:

providing an apparatus comprising:

a radiation source;

a polarizer;

a photoelastic modulator;

a multichannel detector having a plurality of detection elements configured to simultaneously generate a detection value at each detection element; and a processor for processing the simultaneously generated detection values to determine a plurality of measurements, each measurement corresponding with a respective detection element and being indicative of a change induced by the film on the sample on the irradiation beam;

irradiating the sample with a polarized irradiation beam;

linearly polarizing a return beam from the sample;

modulating the irradiation or return beam with a birefringence modulator in accordance with a primary modulation signal;

generating a secondary modulation signal which has a predetermined phase relationship with the primary modulation signal;

directing the return beam onto a multichannel detector, the multichannel detector having a plurality of detection elements;

simultaneously generating a detection value at each detection element;

processing the simultaneously generated detection values to determine a plurality of measurements, each measurement corresponding with a respective detection element and being indicative of a change induced by the film on the sample on the irradiation beam;

modulating the irradiation or return beam in accordance with the secondary modulation signal, or controlling the generation or processing of the detection values in accordance with the secondary modulation signal; and determining, using at least the plurality of measurements, the thickness of the film.

32. A method of measuring a characteristic of a sample, including:

providing an apparatus comprising:

a radiation source;

a polarizer;

a birefringence modulator configured to modulate an irradiation or return beam in accordance with a primary modulation signal;

an analyzer;

a multichannel detector having a plurality of detection elements configured to simultaneously generate a detection value at each detection element, the detector having a response time greater than a period of the primary modulation signal; and a processor for processing the simultaneously generated detection values to determine a plurality of measurements, each measurement corresponding with a respective detection element and being indicative of a change induced by the sample on the irradiation beam;

irradiating the sample with a polarized irradiation beam;

linearly polarizing a return beam from the sample;

modulating the irradiation or return beam with a birefringence modulator in accordance with a primary modulation signal;

generating a secondary modulation signal which has a predetermined phase relationship with the primary modulation signal;

directing the return beam onto a multichannel detector, the multichannel detector having a plurality of detection elements;

simultaneously generating a detection value at each detection element;

processing the simultaneously generated detection values to determine a plurality of measurements, each measurement corresponding with a respective detection element and being indicative of a change induced by the sample on the irradiation beam;

modulating the irradiation or return beam in accordance with the secondary modulation signal, or controlling the generation or processing of the detection values in accordance with the secondary modulation signal; and determining, using at least the plurality of measurements, the characteristic of the sample.

33. A method of performing a measurement on a sample to determine a thickness of a film on the sample of claim 1, including:
performing two or more measurements on a sample, one or more of the measurements being performed using a first set of analyzer and polarizer angles, $A_1$, and $P_1$ and one or more of the measurements being performed using a second set of analyzer and polarizer angles, $A_2$ and $P_2$;
wherein the first and second sets of analyzer and polarizer angles are chosen such that $\tan A_2 \tan P_2 = -\tan A_1 \tan P_1$, and combining the results of the measurements to determine ellipticity parameters.

34. A method according to claim 12 wherein the irradiation or return beam is modulated in accordance with the secondary modulation signal by opening and closing a gate in the path of the beam.

35. A method according to claim 34 wherein the secondary modulation signal is arranged to omit at least a portion of the spectral response of the radiation source related to heating and cooling effects of the radiation source.

* * * * *